(12) United States Patent
O'Heeron et al.

(10) Patent No.: US 11,034,934 B2
(45) Date of Patent: Jun. 15, 2021

(54) METHODS OF ENHANCING FIBROBLAST THERAPEUTIC ACTIVITY

(71) Applicant: SpinalCyte, LLC, Houston, TX (US)

(72) Inventors: Pete O'Heeron, Houston, TX (US); Thomas Ichim, San Diego, CA (US); Kristin Comella, Weston, FL (US)

(73) Assignee: SpinalCyte, LLC, Houston, TX (US)

( * ) Notice: Subject to any disclaimer, the term of this patent is extended or adjusted under 35 U.S.C. 154(b) by 0 days.

(21) Appl. No.: 15/868,420

(22) Filed: Jan. 11, 2018

(65) Prior Publication Data

US 2018/0195044 A1 Jul. 12, 2018

Related U.S. Application Data

(60) Provisional application No. 62/445,133, filed on Jan. 11, 2017.

(51) Int. Cl.
*C12N 5/077* (2010.01)
*A61K 35/33* (2015.01)
*C12N 5/074* (2010.01)

(52) U.S. Cl.
CPC ............ *C12N 5/0656* (2013.01); *A61K 35/33* (2013.01); *C12N 5/0696* (2013.01); *C12N 2501/113* (2013.01); *C12N 2501/115* (2013.01); *C12N 2501/15* (2013.01); *C12N 2502/115* (2013.01)

(58) Field of Classification Search
CPC .............................. C12N 5/0656; C12N 5/077; C12N 2502/115; C12N 2501/115; C12N 2501/15; C12N 2501/113; C12N 5/0696; A61K 35/33
See application file for complete search history.

(56) References Cited

U.S. PATENT DOCUMENTS

| | | | |
|---|---|---|---|
| 6,328,762 B1 * | 12/2001 | Anderson .......... | A61K 48/0075 623/1.1 |
| 9,138,460 B2 | 9/2015 | Sevrain et al. | |
| 2001/0038848 A1 | 11/2001 | Donda et al. | |
| 2009/0274627 A1 | 11/2009 | Yamada et al. | |
| 2010/0209404 A1 | 8/2010 | Hong | |
| 2014/0044682 A1 | 2/2014 | O'Heeron | |
| 2014/0314726 A1 | 10/2014 | O'Heeron et al. | |
| 2014/0356893 A1 * | 12/2014 | Mishra ................. | C12N 5/0696 435/29 |
| 2014/0377231 A1 | 12/2014 | O'Heeron | |
| 2016/0220699 A1 | 8/2016 | O'Heeron | |

FOREIGN PATENT DOCUMENTS

| | | | | |
|---|---|---|---|---|
| WO | WO-2004024198 A1 * | 3/2004 | ............ | A61L 27/38 |
| WO | 2017123951 A1 | 7/2017 | | |
| WO | 2018/195308 A1 | 10/2018 | | |
| WO | 2019/108756 A1 | 6/2019 | | |
| WO | 2019/125996 A1 | 6/2019 | | |

OTHER PUBLICATIONS

Li et al. Skin Biopsy and Patient-Specific Stem Cell Lines. Methods in Molecular Biology (epub Jul. 2015), vol. 1353, p. 77-88, online ISBN: 978-1-4939-3034-0. (Year: 2015).*
Byrne et al. Enhanced Generation of Induced Pluripotent Stem Cells from a Subpopulation of Human Fibroblasts. PLoS One (2009), 4(9), e7118, 9 pages. (Year: 2009).*
Ramos-Torrecillas et al. Human Fibroblast-Like Cultures in the Presence of Platelet-Rich Plasma as a Single Growth Factor Source : Clinical Implications. Adv Skin Wound Care (2014), 27, 114-120. (Year: 2014).*
Pochini et al Analysis of cytokine profile and growth factors in platelet-rich plasma obtained by open systems and commercial columns. einstein (2016), 14(3), 391-397. (Year: 2016).*
Chee et al. Cell Therapy with Human Dermal Fibroblasts Enhances Intervertebral Disk Repair and Decreases Inflammation in the Rabbit Model. Global Spine Journal (Apr. 2016), 6(8), 771-779. (Year: 2016).*
Pham et al. Production of endothelial progenitor cells from skin fibroblasts by direct reprogramming for clinical usages. In Vitro Cell Dev Biol (epub Oct. 2016), 53, 207-216. (Year: 2016).*
Iio et al. Hyaluronic acid induces the release of growth factors from platelet-rich plasma. Asia Pac J Sports Med Arthrosc Rehabil Technol (epub Feb. 2016), 4, 27-32. (Year: 2016).*
Nieuwenhuizen, L., et al; "Stimulation of Naive Monocytes and PBMCs with Coagulation Proteases Results in Thrombin-Mediated and PAR-1-Dependent Cytokine Release and Cell Proliferation in PBMCs Only"; Experimental Immunology; Scandinavian Journal of Immunology; 2013 Blackwell Publishing Ltd., pp. 339-349.
Sarbjeet Makkar, et al; "Hyaluronic Acid Binding to TLR4 Promotes Proliferation and Blocks Apoptosis in Colon Cancer"; Molecular Cancer Therapeutics; 18(12) Dec. 2019, pp. 2446-2456.
S. Kushida, "Effects of platelet-rich plasma on proliferation and myofibroblastic differentiation in human dermal fibroblasts." Ann Plast Surg. Aug. 2013; 71(2):219-24.

(Continued)

*Primary Examiner* — Sean C. Barron
(74) *Attorney, Agent, or Firm* — Norton Rose Fulbright US LLP

(57) ABSTRACT

Disclosed are compositions of matter, cells, protocols and procedures useful for augmentation of one or more therapeutic activities of fibroblast cellular populations. In one embodiment fibroblasts are pretreated with growth factor-comprising composition(s), wherein the growth factor(s) may be cytokines, peptides, and/or proteins. In another embodiment fibroblasts are cultured with platelet rich plasma and/or derivatives from platelet rich plasma. In another embodiment, fibroblasts are cultured under hypoxic conditions prior to administration to an individual. The disclosure further provides means of assessment of fibroblast activity in vitro, including wound repair assay and cytokine production, for example.

13 Claims, 3 Drawing Sheets

(56) References Cited

OTHER PUBLICATIONS

Croft et al: "Rheumatoid synovial fibroblasts differentiate into distinct subsets in the presence of cytokines and cartilage", Arthritis Research & Therapy, vol. 18, no. I, Nov. 18, 2016 (Nov. 18, 2016).
Dasu et al: "Matrix metalloproteinase expression in cytokine stimulated human dermal fibroblasts", BURNS., vol. 29, No. 6, Sep. 1, 2003 (Sep. 1, 2003), pp. 527-531.
Elias et al: "Transforming growth factor-beta regulation of IL-6 production by unstimulated and IL-1-stimulated human fibroblasts [published erratum appears in J Immunol Aug. 15, 1991;147(4):1460]", The Journal of immunology (1950), May 15, 1991 (May 15, 1991), pp. 3437-3443.
Kakudo et al: "Proliferation-Promoting Effect of Platelet-Rich Plasma on Human Adipose-Derived Stem Cells and Human Dermal Fibroblasts", Plastic and Reconstructive Surgery, vol. 122, No. 5, Nov. 1, 2008 (Nov. 1, 2008), pp. 1352-1360.
Tomohiro Kato et al: "Exosomes from stimulated synovial fibroblasts induce osteoarthritic changes in articular chondrocytes", Arthritis Research and Therapy, vol. 16, No. 4, Aug. 4, 2014 (Aug. 4, 2014), p. R163, Biomed Central, London, GB.
Pochini et al., "Analysis of cytokine profile and growth factorsin platelet / rich plasma obtained by open systems and commercial columns.", Einstein (Sao Paulo). Jul.-Sep. 2016;14(3):391-397.
Byrne, et al. "Enhanced generation of induced pluripotent stem cells from a subpopulation of human fibroblasts." PloS one vol. 4,9 e7119. Sep. 23, 2009.
Toru Hino "Hino Lights, Biologically active compounds and Physiologically active substances," 1998, 34 , vol. 7, No. 716 to 717, Publication date Aug. 26, 2018, Online ISSN 2189, Publication date : 7026, Print ISSN 0014 / 8601, https://doi.org/10.14894/faruawpsj.34.7_716_2, https://www.jstage.jst.go.jp/article/faruawpsj/347/34_KJ00001720319/_article/-char/ja.

* cited by examiner

METHODS OF ENHANCING FIBROBLAST THERAPEUTIC ACTIVITY

CROSS-REFERENCE TO RELATED APPLICATIONS

This application claims the benefit of U.S. Provisional Application 62/445,133 filed on Jan. 11, 2017, which is incorporated by reference herein in its entirety.

TECHNICAL FIELD

Embodiments of the disclosure concern at least the fields of cell biology, molecular biology, biochemistry, and medicine.

BACKGROUND

Musculoskeletal disorders of the spine are an extremely common occurrence associated with debilitating back pain, leading to enormous psychosocial and economic ramifications. Lower-back pain is the leading source of disability in people under 45 years of age, and it results in significant economic losses [1]. 80% of people in the United States will experience back pain at some point in their lifetime [2], and it is the second most common reason for symptomatic physician visits [3]. Causes of back pain range from injury-induced, which presents as a minor problem, accelerating to a chronic disorder, as well as degenerative spine diseases that lead to degenerative spondylolisthesis and spinal stenosis. The vast majority of chronic back pain is associated with degeneration of the intervertebral disc, which can manifest in many different clinical conditions including spinal stenosis and instability, radiculopathy, myelopathy, and disc herniation.

Although the association between disc degeneration and chronic back pain is established, the fact is that disc degeneration can occur without back pain. It is known that disc degeneration occurs as a natural process, in many individuals asymptomatically. The origin of pain has therefore been termed "discogenic" not necessarily because of the disc degenerative process, but in part due to the granulation tissue that invades the disc space and causes inflammation and nociception [4].

There is a prevalent view that the majority of lower back pain that is associated with disc degeneration is caused by nerve root compression (radiculopathic pain); however, magnetic resonance imaging many times does not detect compression of verves, even in patients that have sciatica [5]. More recent studies suggest that lumbar disc herniation itself is not the major cause of lower back pain, but instead the discogenic pain is caused by annular disruption, such as an annular tear [6-9]. The fact that the annulus itself is surrounded by various nerve endings allows the possibility that inflammation associated with the disruptions of the annular rings is what triggers pain [10].

Broadly speaking, disc degeneration begins as early as the first decade of life when various biochemical changes become apparent in the endplate and the nucleus pulposus [11]. Subsequently, in the second decade notochordal cells begin undergoing replacement by chondrocytes. In the third decade loss of the fine fibrous connective tissue network and replacement by hyalinized collagen fibers occurs, with concurrent initiation of fissures in the annulus fibrosis. Beginning in the fourth decade and almost always present in the fifth is replacement of the nucleus pulposus jelly-like substance with a fibrous collagen type II structure that resembles the annulus fibrosis. By the seventh decade the nucleus pulposus is completely devoid of the water carrying proteoglycan mass and instead is empty or filled with amorphous material. During this natural process the cartilage endplate, which contains blood vessels for the annular fibrosis and nucleus pulposus becomes replaced with fibrocartilage and blood flow progressively diminishes. Since the only 2 routes for the exchange of solutes with the blood vessels outside the disk are via the periphery of the annulus, and through the end-plates, the natural degeneration of the endplate blood supply causes a decrease ability of nucleus pulposus cells to function/survive, thus leading to decreased proteoglycan synthesis and disc degeneration [12].

The synthesis of proteoglycans in the nucleus pulpous occurs naturally by the cellular component of the nucleus pulposus. Specific growth factors such as TGF-b and EGF are involved in the stimulation of proteoglycan synthesis. Interestingly in patients with degenerative disc disease the amount of these cytokines is reduced in comparison to healthy nucleus pulposus cells [13]. Another reason for inhibition of proteoglycan synthesis is lower pH caused by ischemia of the lumbar area [14]. On the other hand, it is known that matrix metalloproteases are involved in cleaving proteoglycans, and that upregulation of matrix metalloprotease activity is associated with disc degeneration [15]. Activation of matrix metalloproteases is known to be induced by inflammatory cytokines such as TNF and IL-1 [16]. Additionally, animal studies have demonstrated that hyperphysiological loading of the disc segment induces upregulation of matrix metalloproteases [17].

Therefore it appears that lower back pain, at least in a large proportion of patients, is caused by an inflammatory event that occurs in conjunction with lumbar disc degeneration. The link between inflammation and pain is established in studies showing that radiologically degenerated discs are not associated with main in a large number of subjects. In contrast, the presence of localized inflammation associated with disc degeneration, as exemplified by the presence of granulation tissue which is believed to be causative of nociception and the symptoms of chronic, intractable, lower back pain [10, 18].

Although disc degeneration continues to have a tremendous and ever-increasing impact worldwide, current treatment options do not address the underlying cause. These include bed rest, nonsteroidal anti-inflammatory medication in the early phases of pathology, and procedures such as discectomy, arthroplasty (joint replacement), injection of artificial nucleus pulposus and fusion in the later phases when the prior approaches did not ameliorate pain. Approaches such as the previously mentioned not only are unpredictable, but also deal almost exclusively with end-stage clinical manifestations, and therefore do nothing to alter the disease process itself. Additionally, procedures such as vertebral fusion result in the increased incidence of disc degeneration in the adjacent discs due to alterations in the biomechanical distribution of work-load.

Recent advances in both biotechnology and our understanding of the biochemical makeup and environment of the intervertebral disc have led to increased interest in the process of degeneration and the possibility of developing novel treatments aimed directly at disc preservation. Certain genes found to have significant impact on matrix synthesis and catabolism within the disc have provided targets for scientists seeking to alter the balance between the two. To this end, much attention over the past several years has centred on gene therapy, and these efforts have yielded promising preclinical results with regard to its use in treating disc degeneration [19].

Currently, no biologic treatment is widely available for disc degeneration. However, many different molecules of potential therapeutic benefit are being investigated. The focus of molecular therapy has been to prevent or reverse one or more aspects of these changes in the disc extracellular matrix. At least four different classes of molecules may be effective in disc repair. These include anticatabolics, mitogens, chondrogenic morphogens and intracellular regulators [20-22].

As mentioned above, hallmarks of disc degeneration include loss of proteoglycan, water, and Type II collagen in the disc matrix. Furthermore, qualitative changes in the matrix are less well defined, including loss of the higher molecular weight proteoglycans, and other changes that are more difficult to quantify (collagen cross-linking, organization of the proteoglycan, etc.). An important process in disc degeneration seems to be the change of the differentiated chondrocyte phenotype in the nucleus pulposus into a more fibrotic phenotype. Together these changes in the disc matrix lead to alteration of the disc and vertebral anatomy that ultimately is associated with a pathologic condition [23, 24].

Because matrix loss is a balance between matrix synthesis and degradation, it is possible to increase disc matrix by increasing synthesis or by decreasing degradation. One approach is to prevent matrix loss by inhibiting the degradative enzymes.

Degenerated discs have elevated concentrations of matrix metalloproteinases (MMPs). Within the matrix, MMP activity is normally inhibited by tissue inhibitors of MMPs (TIMPs) [25-27]. Wallach et al tested whether one of these anticatabolic molecules, TIMP-1, could increase the accumulation of matrix proteoglycans with in vitro experiments. The researchers found that indeed TIMP-1 expression in disc cells increased accumulation and also increased the "measured synthesis rate" of proteoglycans [27].

Chondrogenic morphogens are cytokines that not only possess mitogenic capability but are characterized by their ability to increase the chondrocyte-specific phenotype of the target cell. Most of the research in chondrogenic morphogens has been with transforming growth factor-b (TGF-b), bone morphogenetic proteins (BMPs) or growth and differentiation factors (GDFs). Chondrogenic morphogens are particularly attractive because they may reverse the fibrotic phenotype of disc cells to the more chondrocyte phenotype of disc nucleus cells in younger and more "normal" discs. By definition, these molecules are secreted molecules and hence can potentially act in autocrine, paracrine and endocrine fashion. TGF-b1 is one of the first disc morphogenic molecules to be studied. Thompson et al. reported that TGF-b1 was a mitogen but also showed that it was a highly anabolic molecule leading to significantly increased proteoglycan synthesis per cell. Gene transfer of TGF-b using an adenoviral/CMV vector was capable of reversing radiological signs of disc degeneration in a rabbit model [28].

BMP-2 is another prototypic chondrogenic morphogen [29]. Yoon et al. reported that recombinant human BMP-2 increased production of rat disc cell proteoglycan and significantly increased the chondrocyte phenotype of the disc cells as shown by increased aggrecan and Type II collagen gene expression, whereas there was no change in Type I collagen gene expression [30]. Kim et al. reported that BMP-2 can partially reverse the inhibitory effect of nicotine on the synthesis of disc cell proteoglycan [31]. BMP-7, also known as OP-1 (osteogenic protein-1), is another disc cell morphogen that has demonstrated potent in vitro activity in terms of enhancing matrix formation in disc cells [32-34]. GDF-5 is also known as CDMP-1 is also considered for regeneration of disc cells, although only in vitro experimentation has occurred [35].

The present disclosure concerns methods and compositions that satisfy a long-felt need in the art for degenerative disc repair.

BRIEF SUMMARY

The present disclosure is directed to methods and compositions related to certain cells useful for therapy in an individual, such as therapy in one or more discs of a mammal. In specific embodiments, the cells are fibroblasts that in particular cases have been modified upon exposure to one or more biologically active substance and/or one or more conditions. In certain embodiments the exposure improves one or more therapeutic activities compared to fibroblasts that lack the exposure. Although any particular therapeutic activity of the fibroblasts may be enhanced upon one or more exposures to one or more biologically active substance and/or one or more conditions, in some cases the activity is anti-inflammatory, angiogenic, regenerative and/or disc-regenerating properties, as examples. In specific cases wherein the fibroblasts have improved activities, the fibroblasts are directly or indirectly the cause of amelioration of at least one symptom of a medical condition related to one or more discs of an individual.

In particular embodiments, methods of the disclosure directly or indirectly result in an increase disc matrix, including by increasing synthesis in the disc, by decreasing degradation, and/or by preventing matrix loss by inhibiting degradative enzymes.

In one embodiment, methods are provided for augmenting efficacy of fibroblasts for regeneration of cells and/or tissues, comprising the steps of (optionally) obtaining fibroblast cells; contacting fibroblasts with one or more biologically active substances; and/or culturing the fibroblasts under conditions to enhance efficacy of the fibroblasts for regeneration of the cells and/or tissues. In specific embodiments, the one or more biologically active substances comprise one or more cytokines, such as growth factors (for example, FGF-alpha, FGF-beta, and/or a member of the TGF-beta family). In specific cases, the one or more biologically active substances comprise platelet rich plasma. In particular embodiments, regeneration of cells and/or tissue by the fibroblasts comprises immune modulation, angiogenesis, regeneration of spinal discs, a combination thereof, and so forth.

The fibroblast cells being utilized may be selected from the group consisting of (a) fibroblasts obtained by biopsy, cultured and proliferated; (b) subsets thereof having greater ability to differentiate; and (c) a combination thereof. In specific cases, the fibroblasts express stage specific embryonic antigen 3 (SSEA3). In certain cases, the fibroblasts are comprised in a pharmaceutically acceptable carrier selected from the group consisting of sterile solutions, hydrogels, implantable cell matrices, devices and a combination thereof.

Embodiments of the disclosure include methods for increasing PD-1L expression in fibroblasts, suppressing T-cell activation by fibroblasts, and/or suppressing T-cell production of one or more factors, such as interferon gamma, by fibroblasts.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

I. Examples of Definitions

Figure 1:
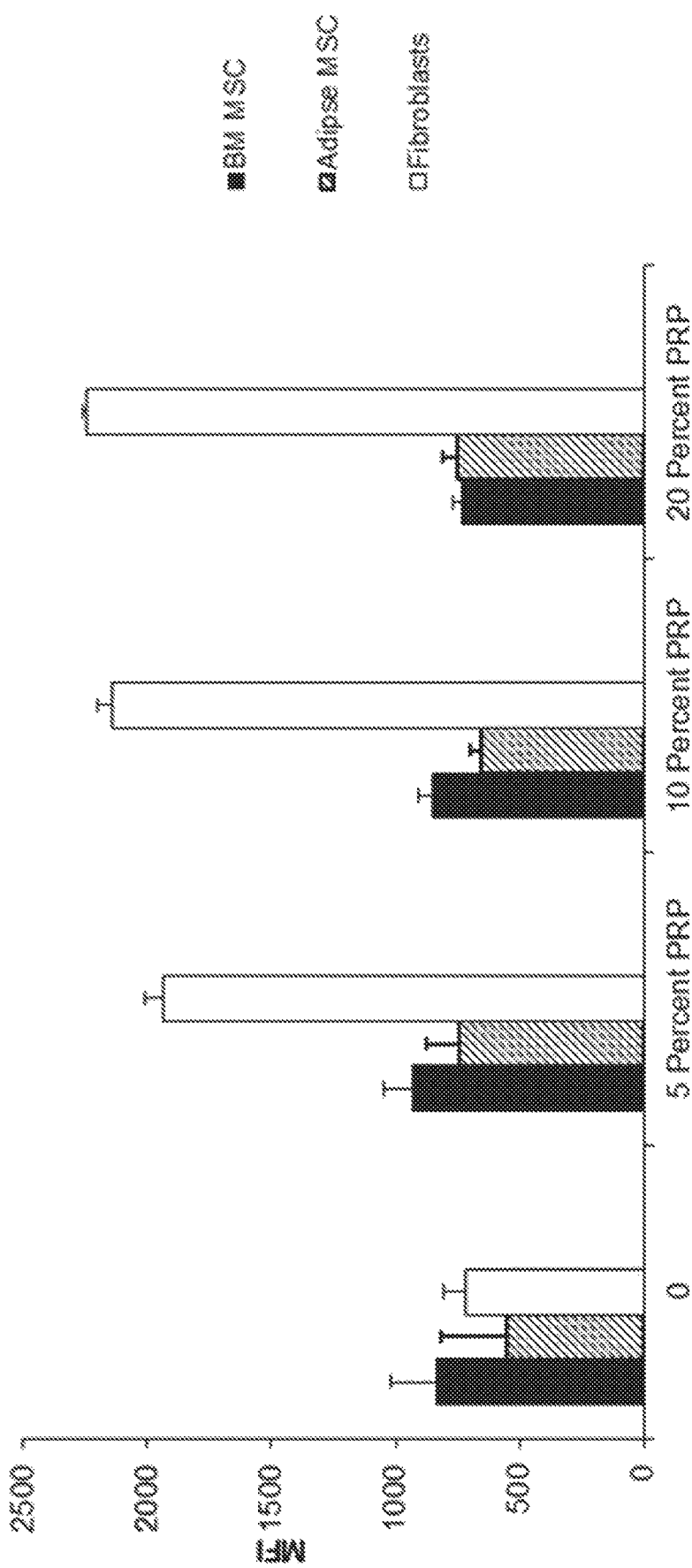
FIG. 1 shows the effects of increasing amounts of platelet rich plasma on PD-1L expression in fibroblasts.
Figure 2:
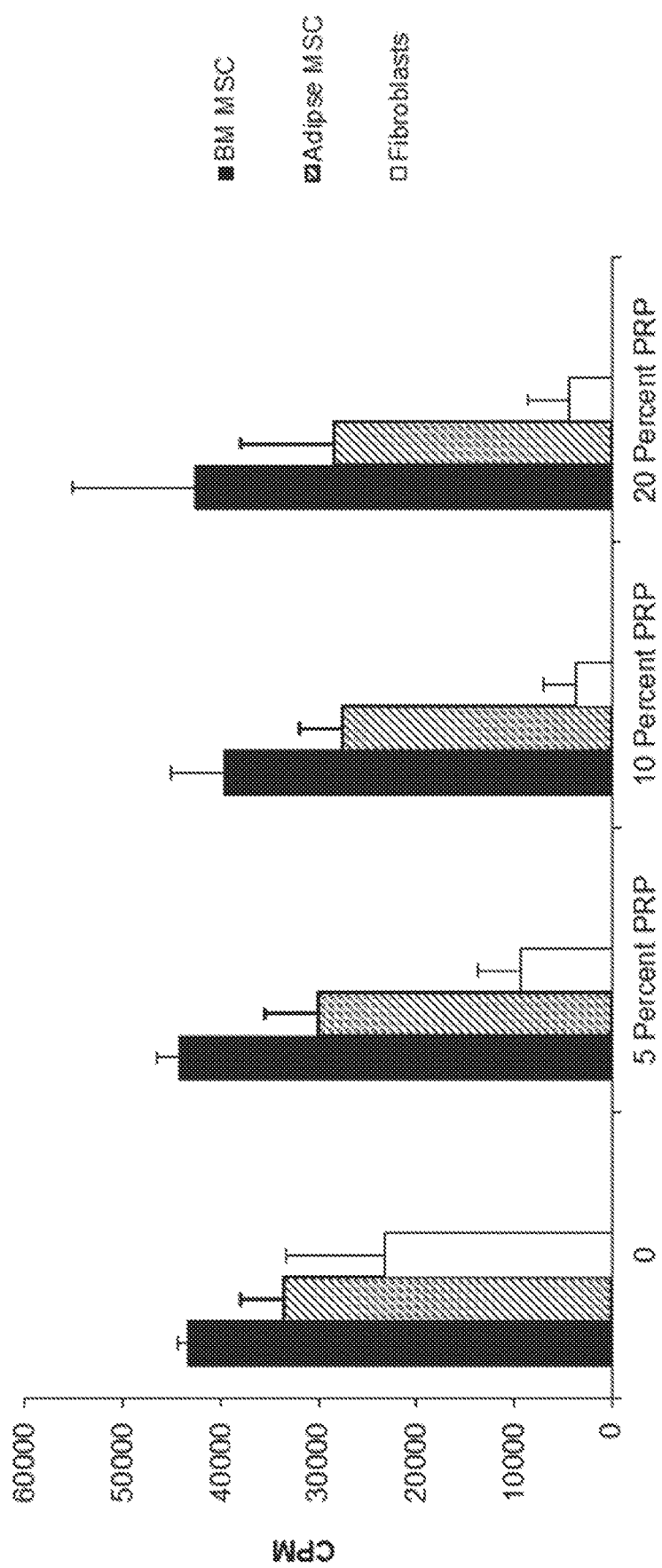
FIG. 2 shows the effects of increasing amounts of platelet rich plasma on suppression of T cell activation by fibroblasts.
Figure 3:
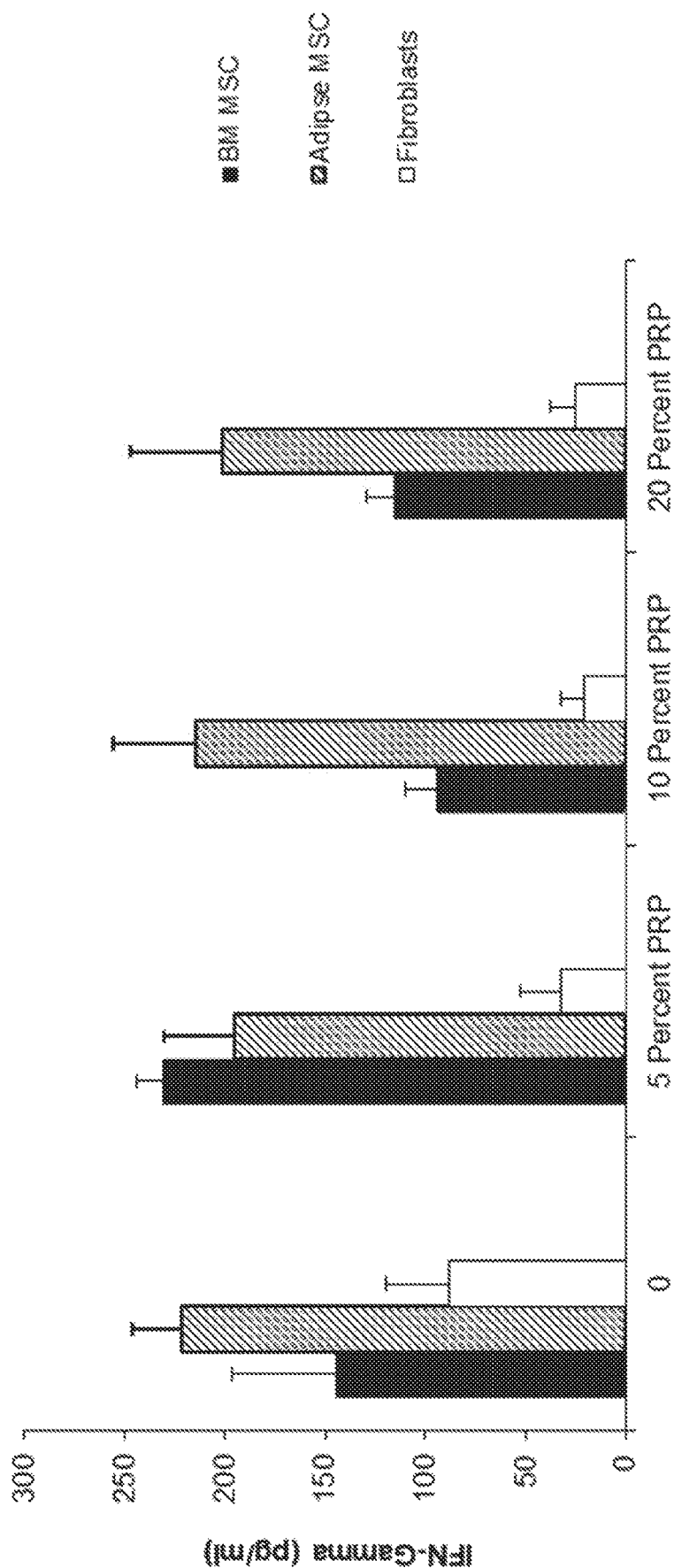
FIG. 3 demonstrates the effects of increasing amounts of platelet rich plasma on suppression of T cell production of interferon gamma by fibroblasts.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

"Biocompatible polymers" used in the present disclosure are selected from the group consisting of carbomers (acrylic acid polymers crosslinked with a polyalkenyl polyether), polyalkylene glycols (for example, polyethylene glycols and polypropylene glycols), poloxamers (polyoxyethylene-polyoxypropylene block copolymers), polyesters, polyethers, polyanhydrides, polyacrylates, polyvinyl acetates, polyvinyl pyrrolidones, and polysaccharides such as, for example, hyaluronic acid, derivatives of hyaluronic acid, in particular crosslinked hyaluronic acid and esters of hyaluronic acid (for example, benzyl ester of hyaluronic acid), hydroxyalkylcelluloses (for example, hydroxymethylcellulose and hydroxyethylcellulose), and carboxyalkylcelluloses (for example, carboxymethylcellulose).

"Growth factor" refers to any material or materials having a positive reaction on living tissues, such as promoting the growth of tissues. Exemplary growth factors include, but are not limited to, platelet-derived growth factor (PDGF), platelet-derived angiogenesis factor (PDAF), vascular endothelial growth factor (VEGF), platelet-derived epidermal growth factor (PDEGF), platelet factor 4 (PF-4), transforming growth factor beta. (TGF-B), acidic fibroblast growth factor (FGF-A), basic fibroblast growth factor (FGF-B), transforming growth factor A (TGF-A), insulin-like growth factors 1 and 2 (IGF-1 and IGF-2), B thromboglobulin-related proteins (BTG), thrombospondin (TSP), fibronectin, von Wallinbrand's factor (vWF), fibropeptide A, fibrinogen, albumin, plasminogen activator inhibitor 1 (PAI-1), osteonectin, regulated upon activation normal T cell expressed and presumably secreted (RANTES), gro-A, vitronectin, fibrin D-dimer, factor V, antithrombin III, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), Keratinocyte Growth Factor-2 (KGF-2), and combinations thereof. One of the important characteristics common to the above listed growth factors is that each substance is known or believed to have a positive reaction on living tissue, known as bioactivity, to enhance cell or tissue growth.

The term "regeneration" as used herein refers to the growth of new cells and/or tissue in an area, such as a damaged area, including a spinal disc.

The term "therapeutically effective amount" as used herein refers to that amount which, when administered to an individual for treating a disease, is sufficient to effect such treatment for the disease, including to ameliorate at least one symptom of the disease.

II. General Embodiments

The disclosure concerns means of augmenting therapeutic activity of fibroblasts, such as fibroblasts that are used at least for anti-inflammatory, angiogenic, regenerative and/or disc-regenerating properties at one or more sites in vivo. In one embodiment of the disclosure, fibroblasts are cultured with cytokines, growth factors, peptides, or combinations thereof prior to administration to an individual, such as a mammal, including humans, horses, dogs, cats, and so forth. In another embodiment, the disclosure encompasses augmentation of regenerative activities for fibroblasts to be used as therapeutic agents, for example through culture (before and/or during administration to an individual) with one or more agents, such as platelet rich plasma (PRP). In another embodiment the disclosure provides methods for enhancing one or more fibroblast activities for therapeutic activity by co-administering one or more agents and/or PRP, for example together with the fibroblasts. In particular cases the enhanced fibroblasts are delivered to an individual for the purpose of treating a disc medical condition in the individual. In some cases an individual is determined to be in need of the enhanced fibroblasts, such as because of a damaged disc or risk thereof. An individual at risk is one that is over the age of about 40, 45, 50, 55, 60, 65, 70, 75, 80, and so forth; an individual that is or was an athlete; an individual with a vocation that requires physical activity; an individual with a spinal injury; or a combination thereof).

In some embodiments, the fibroblasts are exposed to platelet-rich plasma and such exposure directly or indirectly results in enhanced fibroblasts. Numerous growth factors, cytokines and peptides are released from activated platelets, and one approach to therapeutically leverage this is to utilize an autologous platelet concentrate suspended in plasma, also known as platelet-rich plasma (PRP). Several means of preparing PRP are known in the art, some of which are described in the following and incorporated by reference herein [36, 37]. Examples of devices used for generation of PRP include SmartPReP, 3iPCCS, Sequestra, Secquire, CATS, Interpore Cross, Biomet GPS, and Harvest's BMAC [38], for example. Other means of generating PRP are described in U.S. Pat. Nos. 5,585,007; 5,599,558; 5,614,204; 6,214,338; 6,010,627; 5,165,928; 6,303,112; 6,649,072; and 6,649,072, which are incorporated by reference herein in their entirety. In specific embodiments, one can dose PRP at the time of injection in the individual, such as without a prior culture with the fibroblasts.

In one embodiment of the disclosure, fibroblasts are delivered systemically or locally to an individual in need thereof, including an individual in need of treatment, including by using a carrier (for example, hydrogel) comprising platelet rich plasma (PRP) and/or hyaluronic acid (HA); in particular cases PRP and/or HA are blended with batroxobin (BTX) as gelling agent. The fibroblasts may be encapsulated in a hydrogel, such as PRP/HA/BTX hydrogel, and cultured, for example in both growing medium and/or medium with or without TGF-01 (for example) for a certain duration of time, such as from one minute (min) up to 21 days. A range of culture duration for any cells may be from 1, 2, 3, 4, 5, 6, 7, 8, 9, 10, 15, 20, 25, 30, 35, 40, 45, 50, 55, 60 (or more minutes or from 1, 2, 3, 4, 5, 6, 7, 8, 9, 10, 11, 12, 13, 14, 15, 16, 17, 18, 19, 20, 21, 22, 23, or 24 or more hours) to 1, 2, 3, 4, 5, 6, 7, 8, 9, 10, 11, 12, 13, 14, 15, 16, 17, 18, 19, 20, or 21 days. The range of time may be from 1, 2, 3, 4, 5, 6, 7, 8, 9, 10, 15, 20, 25, 30, 35, 40, 45, 50, 55, 60 or more minutes to 1, 2, 3, 4, 5, 6, 7, 8, 9, 10, 11, 12, 13, 14, 15, 16, 17, 18, 19, 20, 21, 22, 23, or 24 or more hours.

In one embodiment, the hydrogel jellifies at a certain temperature in a certain period of time. The hydrogel may jellify in 10, 11, 12, 13, 14, 15, 16, 17, 18, 19, or 20 minutes or more at 18, 19, 20, 21, 22, 23, 24, 25, or higher ° C. or in 1, 2, 3, 4, 5, or more minutes at 35, 36, 37, 38, 39, or 40 or more ° C. in a manner such that the fibroblasts maintain high cell viability and proliferation. In one embodiment the disclosure encompasses the use of fibroblasts for local delivery (such as by intra-disc injections) in individuals with degenerative disc disease. In such an embodiment, the fibroblasts are cultured in suitable conditions to enhance GAG production, which in at least some cases is achieved by culture with one or more cytokines, such as TGF-beta. Methodologies for growth of mesenchymal stem cells, which may be modified for fibroblast-specific use, are provided in the following reference that is incorporated by reference [39].

The disclosure encompasses the use of activation of fibroblasts prior to therapeutic use, including administration of one or more biologically active substances that act as "regenerative adjuvants" for the fibroblasts. The cells in the formulation may display typical fibroblast morphologies when growing in cultured monolayers. Specifically, cells may display an elongated, fusiform or spindle appearance with slender extensions, or cells may appear as larger, flattened stellate cells that may have cytoplasmic leading edges. A mixture of these morphologies may also be observed. The cells may express one or more proteins characteristic of normal fibroblasts including the fibroblast-specific marker, CD90 (Thy-1), a 35 kDa cell-surface glycoprotein, and the extracellular matrix protein, collagen, as examples. The fibroblast dosage formulation in specific embodiments may be an autologous, allogeneic, or xenogeneic cell therapy product comprising a suspension of fibroblasts, including grown from skin using standard tissue culture procedures as examples.

III. Examples of Cell Harvesting, Culturing and Expansion Techniques

In certain embodiments, fibroblasts of any kind are utilized in methods for regeneration, and in preparation for (or as part of) these methods, the fibroblasts may be harvested, cultured, and expanded using certain techniques.

The fibroblasts utilized in the disclosure are generated, in one embodiment, by outgrowth from a biopsy of the recipient individual's own skin (in the case of autologous preparations), or skin of one or more healthy donors (for allogeneic preparations), or a combination thereof may be employed. In some embodiments fibroblasts are used from young donors, although in other cases the fibroblasts are not from young donors and may be adults including middle-aged, for example. In another embodiment fibroblasts are transfected with polynucleotides that encode one or more gene products, for example to allow for enhanced growth and overcoming of the Hayflick limit.

Subsequent to derivation of cells, there may be expansion in culture using standard cell culture techniques. Skin tissue (dermis and epidermis layers) may be biopsied from a subject's post-auricular area, although they may come from other regions, such as breast or stomach regions. In one embodiment, the starting material comprises multiple (such as two, three, four, or more) 3-mm punch skin biopsies collected using standard aseptic practices. The biopsies are collected by an individual and placed into a vessel (such as a vial) comprising standard medium, such as comprising sterile phosphate buffered saline (PBS). The biopsies are transferred under appropriate conditions to a manufacturing facility. In one embodiment, after arrival at a manufacturing facility, the biopsy is inspected and, upon acceptance, transferred directly to the manufacturing area. Upon initiation of the process, the biopsy tissue is then washed prior to enzymatic digestion. After washing, a Liberase Digestive Enzyme Solution is added without mincing, and the biopsy tissue is incubated for a suitable time and using a suitable temperature, such as at 37.0±2° C. for one hour. Time of biopsy tissue digestion is a process parameter that can affect the viability and growth rate of cells in culture and be optimized routinely. An example of the process is as follows: Liberase may be used that is a collagenase/neutral protease enzyme cocktail obtained formulated from Lonza Walkersville, Inc. (Walkersville, Md.) and unformulated from Roche Diagnostics Corp. (Indianapolis, Ind.). Alternatively, other commercially available collagenases may be used, such as Serva Collagenase NB6 (Helidelburg, Germany). After digestion, Initiation Growth Media (IMDM, GA, 10% Fetal Bovine Serum (FBS)) is added to neutralize the enzyme, cells are pelleted by centrifugation and resuspended in 5.0 mL Initiation Growth Media. Alternatively, centrifugation is not performed, with full inactivation of the enzyme occurring by the addition of Initiation Growth Media only. Initiation Growth Media is added prior to seeding of the cell suspension into a T-175 cell culture flask for initiation of cell growth and expansion. A T-75, T-150, T-185 or T-225 flask can be used in place of the T-75 flask. Cells are incubated at 37±2.0° C. with 5.0±1.0% $CO_2$ and fed with fresh Complete Growth Media every three to five days. All feeds in the process are performed by removing half of the Complete Growth Media and replacing the same volume with fresh media. Alternatively, full feeds can be performed. Cells should not remain in the T-175 flask greater than 30 days prior to passaging. Confluence is monitored throughout the process to ensure adequate seeding densities during culture splitting. When cell confluence is greater than or equal to 40% in the T-175 flask, they are passaged by removing the spent media, washing the cells, and treating with Trypsin-EDTA to release adherent cells in the flask into the solution. Cells are then trypsinized and seeded into a T-500 flask for continued cell expansion. Alternately, one or two T-300 flasks, One Layer Cell Stack (1 CS), One Layer Cell Factory (1 CF) or a Two Layer Cell Stack (2 CS) can be used in place of the T-500 Flask. Morphology is evaluated at each passage and prior to harvest to monitor the culture purity throughout the culture purity throughout the process. Morphology is evaluated by comparing the observed sample with visual standards for morphology examination of cell cultures. The cells display typical fibroblast morphologies when growing in cultured monolayers. Cells may display either an elongated, fusiform or spindle appearance with slender extensions, or appear as larger, flattened stellate cells which may have cytoplasmic leading edges. A mixture of these morphologies may also be observed. Fibroblasts in less confluent areas can be similarly shaped, but randomly oriented. The presence of keratinocytes in cell cultures is also evaluated. Keratinocytes appear round and irregularly shaped and, at higher confluence, they appear organized in a cobblestone formation. At lower confluence, keratinocytes are observable in small colonies. Cells are incubated at 37±2.0° C. with 5.0.+−.1.0% $CO_2$ and passaged every three to five days in the T-500 flask and every five to seven days in the ten layer cell stack (10CS). Cells should not remain in the T-500 flask for more than 10 days prior to passaging. Quality Control (QC) release testing for safety of the Bulk Drug Substance includes sterility and endotoxin testing. When cell confluence in the T-500 flask is 95%, cells are passaged to a 10 CS culture vessel. Alternately, two Five Layer Cell Stacks (5 CS) or a 10 Layer Cell Factory (10 CF) can be used in place of the 10 CS. 10CS. Passage to the 10 CS is performed by removing the spent media, washing the cells, and treating with Trypsin-EDTA to release adherent cells in the flask into the solution. Cells are then transferred to the 10 CS. Additional Complete Growth Media is added to neutralize the trypsin and the cells from the T-500 flask are pipetted into a 2 L bottle containing fresh Complete Growth Media. The contents of the 2 L bottle are transferred into the 10 CS and seeded across all layers. Cells are then incubated at 37±2.0° C. with 5.0±1.0% $CO_2$ and fed with fresh Complete Growth Media every five to seven days. Cells should not remain in the 10CS for more than 20 days prior to passaging. In one embodiment, the passaged dermal fibroblasts are rendered substantially free of immunogenic proteins present in the culture medium by incubating the expanded fibroblasts for a period of time in protein free medium, Primary Harvest When cell confluence in the 10 CS is 95% or more, cells are harvested. Harvesting is performed by removing the spent media, washing the cells, treating with Trypsin-EDTA to release adherent cells into the solution, and adding additional Complete Growth Media to neutralize the trypsin. Cells are collected by centrifugation, resuspended, and in-process QC testing performed to determine total viable cell count and cell viability.

In some embodiments, when large numbers of cells are required after receiving cell count results from the primary 10 CS harvest, an additional passage into multiple cell stacks (up to four 10 CS) is performed. For additional passaging, cells from the primary harvest are added to a 2 L media bottle containing fresh Complete Growth Media. Re-suspended cells are added to multiple cell stacks and incubated at 37±2.0° C. with 5.0.+−.1.0% $CO_2$. The cell stacks are fed and harvested as described above, except cell confluence must be 80% or higher prior to cell harvest. The harvest procedure is the same as described for the primary harvest above. A *mycoplasma* sample from cells and spent media is collected, and cell count and viability performed as described for the primary harvest above. The method decreases or eliminates immunogenic proteins be avoiding their introduction from animal-sourced reagents. To reduce process residuals, cells are cryopreserved in protein-free freeze media, then thawed and washed prior to prepping the final injection to further reduce remaining residuals. If additional Drug Substance is needed after the harvest and cryopreservation of cells from additional passaging is complete, aliquots of frozen Drug Substance—Cryovial are thawed and used to seed 5 CS or 10 CS culture vessels. Alternatively, a four layer cell factory (4 CF), two 4 CF, or two 5 CS can be used in place of a 5 CS or 10 CS. A frozen cryovial(s) of cells is thawed, washed, added to a 2 L media bottle containing fresh Complete Growth Media and cultured, harvested and cryopreserved as described above. The cell suspension is added Cell confluence must be 80% or more prior to cell harvest.

At the completion of culture expansion, the cells are harvested and washed, then formulated to contain 1.0-2.7× $10^7$ cells/mL, with a target of 2.2×$10^7$ cells/mL. Alternatively, the target can be adjusted within the formulation range to accommodate different indication doses. The drug substance consists of a population of viable, autologous human fibroblast cells suspended in a cryopreservation medium consisting of Iscove's Modified Dulbecco's Medium (IMDM) and Profreeze-CDM™ (Lonza, Walkerville, Md.) plus 7.5% dimethyl sulfoxide (DMSO). Alternatively, a lower DMSO concentration may be used in place of 7.5% or CryoStor™ CS5 or CryoStor™ CS10 (BioLife Solutions, Bothell, Wash.) may be used in place of IMDM/Profreeze/DMSO. In addition to cell count and viability, purity/identity of the Drug Substance is performed and must confirm the suspension contains 98% or more fibroblasts. The usual cell contaminants include keratinocytes. The purity/identify assay employs fluorescent-tagged antibodies against CD90 and CD 104 (cell surface markers for fibroblast and keratinocyte cells, respectively) to quantify the percent purity of a fibroblast cell population. CD90 (Thy-1) is a 35 kDa cell-surface glycoprotein. Antibodies against CD90 protein have been shown to exhibit high specificity to human fibroblast cells. CD104, integrin beta4 chain, is a 205 kDa transmembrane glycoprotein which associates with integrin alpha6 chain (CD49f) to form the alpha6/beta4 complex. This complex has been shown to act as a molecular marker for keratinocyte cells (Adams and Watt 1991).

Antibodies to CD 104 protein bind to 100% of human keratinocyte cells. Cell count and viability is determined by incubating the samples with Viacount Dye Reagent and analyzing samples using the Guava PCA system. The reagent is composed of two dyes, a membrane-permeable dye which stains all nucleated cells, and a membrane-impermeable dye which stains only damaged or dying cells. The use of this dye combination enables the Guava PCA system to estimate the total number of cells present in the sample, and to determine which cells are viable, apoptotic, or dead. The method was custom developed specifically for use in determining purity/identity of autologous cultured fibroblasts. Alternatively, cells can be passaged from either the T-175 flask (or alternatives) or the T-500 flask (or alternatives) into a spinner flask containing microcarriers as the cell growth surface. Microcarriers are small bead-like structures that are used as a growth surface for anchorage dependent cells in suspension culture. They are designed to produce large cell yields in small volumes. In this apparatus, a volume of Complete Growth Media ranging from 50 mL-300 mL is added to a 500 mL, IL or 2 L sterile disposable spinner flask. Sterile microcarriers are added to the spinner flask. The culture is allowed to remain static or is placed on a stir plate at a low RPM (15-30 RRM) for a short period of time (1-24 hours) in a 37±2.0° C. with 5.0±1.0% $CO_2$ incubator to allow for adherence of cells to the carriers. After the attachment period, the speed of the spin plate is increased (30-120 RPM). Cells are fed with fresh Complete Growth Media every one to five days, or when media appears spent by color change. Cells are collected at regular intervals by sampling the microcarriers, isolating the cells and performing cell count and viability analysis. The concentration of cells per carrier is used to determine when to scale-up the culture. When enough cells are produced, cells are washed with PBS and harvested from the microcarriers using trypsin-EDTA and seeded back into the spinner flask in a larger amount of microcarriers and higher volume of Complete Growth Media (300 mL-2 L). Alternatively, additional microcarriers and Complete Growth Media can be added directly to the spinner flask containing the existing microcarrier culture, allowing for direct bead-to-bead transfer of cells without the use of trypsinization and reseeding. Alternatively, if enough cells are produced from the initial T-175 or T-500 flask, the cells can be directly seeded into the scale-up amount of microcarriers. After the attachment period, the speed of the spin plate is increased (30-120 RPM). Cells are fed with fresh Complete Growth Media every one to five days, or when media appears spent by color change. When the concentration reaches the desired cell count for the intended indication, the cells are washed with PBS and harvested using trypsin-EDTA. Microcarriers used within the disposable spinner flask may be made from poly blend such as BioNOC (Cesco Bioengineering, distributed by Bellco Biotechnology, Vineland, N.J.) and FibraCel® (New Brunswick Scientific, Edison, N.J.), gelatin, such as Cultispher-G (Percell Biolytica, Astrop, Sweden), cellulose, such as Cytopore™ (GE Healthcare, Piscataway, N.J.) or coated/uncoated polystyrene, such as 2D MicroHex™ (Nunc, Weisbaden, Germany), Cytodex® (GE Healthcare, Piscataway, N.J.) or Hy-Q Sphere™ (Thermo Scientific Hyclone, Logan, Utah).

In another embodiment, cells can be processed on poly blend 2D microcarriers such as BioNOC II® and FibraCel® using an automatic bellow system, such as FibraStage™. (New Brunswick Scientific, Edison, N.J.) or BelloCell® (Cesco Bioengineering, distributed by Bellco Biotechnology, Vineland, N.J.) in place of the spinner flask apparatus. Cells from the T-175 (or alternatives) or T-500 flask (or alternatives) are passaged into a bellow bottle containing microcarriers with the appropriate amount of Complete Growth Media, and placed into the system. The system pumps media over the microcarriers to feed cells, and draws away media to allow for oxygenation in a repeating fixed cycle. Cells are monitored, fed, washed and harvested in the same sequence as described above. Alternatively, cells can be processed using automated systems. After digestion of the biopsy tissue or after the first passage is complete (T-175 flask or alternative), cells may be seeded into an automated device. One method is an Automated Cellular Expansion (ACE) system, which is a series of commercially available or custom fabricated components linked together to form a cell growth platform in which cells can be expanded without human intervention. Cells are expanded in a cell tower, consisting of a stack of disks capable of supporting anchorage-dependent cell attachment. The system automatically circulates media and performs trypsinization for harvest upon completion of the cell expansion stage.

Alternatively, the ACE system can be a scaled down, single lot unit version comprised of a disposable component that consists of cell growth surface, delivery tubing, media and reagents, and a permanent base that houses mechanics and computer processing capabilities for heating/cooling, media transfer and execution of the automated programming cycle. Upon receipt, each sterile irradiated ACE disposable unit will be unwrapped from its packaging and loaded with media and reagents by hanging pre-filled bags and connecting the bags to the existing tubing via aseptic connectors. In specific embodiments, the process continues as follows: a) Inside a biological safety cabinet (BSC), a suspension of cells from a biopsy that has been enzymatically digested is introduced into the "pre-growth chamber" (small unit on top of the cell tower), which is already filled with Initiation Growth Media containing antibiotics. From the BSC, the disposable would be transferred to the permanent ACE unit already in place; b) After approximately three days, the cells within the pre-growth chamber are trypsinized and introduced into the cell tower itself, which is pre-filled with Complete Growth Media. Here, the "bubbling action" caused by $CO_2$ injection force the media to circulate at such a rate that the cells spiral downward and settle on the surface of the discs in an evenly distributed manner; c) For approximately seven days, the cells are allowed to multiply. At this time, confluence will be checked (method unknown at time of writing) to verify that culture is growing. Also at this time, the Complete Growth Media will be replaced with fresh Complete Growth Media. CGM will be replaced every seven days for three to four weeks. At the end of the culture period, the confluence is checked once more to verify that there is sufficient growth to possibly yield the desired quantity of cells for the intended treatment; d) If the culture is sufficiently confluent, it is harvested. The spent media (supernatant) is drained from the vessel. PBS will then is pumped into the vessel (to wash the media, FBS from the cells) and drained almost immediately. Trypsin-EDTA is pumped into the vessel to detach the cells from the growth surface. From the spin separator, the cells will be sent through an inline automated cell counting device or a sample collected for cell count and viability testing via laboratory analyses. Once a specific number of cells has been counted and the proper cell concentration has been reached, the harvested cells are delivered to a collection vial that can be removed to aliquot the samples for cryogenic freezing.

In another embodiment, automated robotic systems may be used to perform cell feeding, passaging, and harvesting for the entire length or a portion of the process. Cells can be introduced into the robotic device directly after digest and seed into the T-175 flask (or alternative). The device may have the capacity to incubate cells, perform cell count and viability analysis and perform feeds and transfers to larger culture vessels. The system may also have a computerized cataloging function to track individual lots. Existing technologies or customized systems may be used for the robotic option.

A party that obtains the fibroblasts may or may not be a party that manipulates the fibroblasts to produce their enhancement and/or deliver them to an individual.

IV. Examples of Fibroblasts and Manipulation Thereof

Following the obtaining and preparation of fibroblasts prior to delivery to an individual in need thereof, the fibroblasts may be manipulated, including to enhance one or more activities useful for a therapeutic purpose. In some cases, the fibroblasts are exposed to one or more biologically active agents and/or conditions prior to (and/or during) delivery to an individual in need thereof, and in some cases the exposure to one or more biologically active agents and/or conditions prior to (and/or during) delivery may or may not occur during a culturing step.

In one embodiment, fibroblasts are pre-activated by contact with a composition or mixture of compositions comprising a biologically active agent that is at least one growth factor, and the growth factor(s) may be selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and a combination thereof. In certain cases, the growth factors are transforming growth factors (TGF), platelet-derived growth factors (PDGF) fibroblast growth factors (FGF) and a combination thereof. In specific cases, the growth factors are selected from the group consisting of transforming growth factors beta (TGF-beta), platelet-derived growth factors BB (PDGF-BB), basic fibroblast growth factors (bFGF) and a combination thereof. In another embodiment of the disclosure, the growth factor-comprising compositions are delivered to an individual simultaneously with, or subsequent to, delivery of fibroblasts. The delivery may occur by injection, in certain embodiments. The fibroblasts may be autologous, allogeneic, or xenogeneic with respect to the recipient individual. In some embodiments a platelet plasma composition is administered together with the fibroblasts or subsequent to administration of the fibroblasts, and the platelet plasma composition may comprise, consist essentially of, or consist of platelets and plasma and may be derived from bone marrow and/or peripheral blood. The present disclosure may use platelet plasma composition(s) from either or both of these sources, and either platelet plasma composition may be used to regenerate either a nucleus or annulus or both in need thereof. Further, the platelet plasma composition may be used with or without concentrated bone marrow (BMAC). By way of example, when inserted into the annulus, 0.05-2.0 cc of platelet plasma composition may be used, and when inserted into the nucleus, 0.05-3.0 cc of the platelet plasma composition may be used. Platelets are non-nucleated blood cells that as noted above may be found in bone marrow and peripheral blood.

In various embodiments of the present disclosure, a platelet plasma composition may be obtained by sequestering platelets from whole blood and/or bone marrow through centrifugation, for example into three strata: (1) platelet rich plasma; (2) platelet poor plasma; and (3) fibrinogen. When using platelets from one of the strata, e.g., the platelet rich plasma (PRP) from blood, one may use the platelets whole or their contents may be extracted and concentrated into a platelet lysate through a cell membrane lysis procedure using thrombin and/or calcium chloride, for example. When choosing whether to use the platelets whole or as a lysate, one may consider the rate at which one desires regeneration and/or tissue healing (which may include the formation of scar tissue without regeneration or healing of a herniated or torn disc). In some embodiments the lysate will act more rapidly than the PRP (or platelet poor plasma from bone marrow). Notably, platelet poor plasma that is derived from bone marrow has a greater platelet concentration than platelet rich plasma from blood, also known as platelet poor/rich plasma, ("PP/RP" or "PPP"). PP/RP or PPP may be used to refer to platelet poor plasma derived from bone marrow, and in some embodiments, preferably PP/RP is used or PRP is used as part of the composition for disc regeneration. (By convention, the abbreviation PRP refers only to compositions derived from peripheral blood and PPP (or PP/RP) refers to compositions derived from bone marrow.) In various embodiments, the platelet plasma composition, which may or may not be in the form of a lysate, may serve one or more of the following functions: (1) to release/provide growth factors and/or cytokines for tissue regeneration; (2) to reduce inflammation; (3) to attract/mobilize cell signaling; (4) to initiate fibroblast repair of damaged annulus through fibroblast growth factors (FGF); (5) to stabilize disc annulus; (6) to repair annulus disc tears; (7) to stimulate revascularization to a disc; and (8) to stimulate stem cell activation. In some embodiments, by combining platelet therapy with stem cells, there can be synergy with respect to reducing back pain. In any event, the individual may have been receiving, is receiving, or will receive one or more pain relievers of any kind.

In some embodiments in which the lysate is used, the cytokine(s) may be concentrated in order to optimize their functional capacity. Concentration may be accomplished in two steps. First, blood may be obtained and concentrated to a volume that is 5-15% of what it was before concentration. Devices that may be used include but are not limited to a hemofilter or a hemoconcentrator. For example, 60 cc of blood may be concentrated down to 6 cc. Next, the concentrated blood may be filtered to remove water. This filtering step may reduce the volume further to 33%-67% (e.g., approximately 50%) of what it was prior to filtration. Thus, by way of example for a concentration product of 6 cc, one may filter out water so that one obtains a product of approximately 3 cc. When the platelet rich plasma, platelet poor plasma and fibrinogen are obtained from blood, they may for example be obtained by drawing 20-500 cc of peripheral blood, 40-250 cc of peripheral blood or 60-100 cc of peripheral blood. The amount of blood that one should draw will depend on the number of discs that have degenerated and the size of the discs. As persons of ordinary skill in the art will appreciate, a typical disc has a volume of 2-5 cc or 3-4 cc. In one specific embodiment fibroblasts are treated, or administered together with activated PRP. The method of generation of activated PRP may be used according to U.S. Pat. No. 9,011,929, which is incorporated by reference herein in its entirety and describes essentially: separating the PRP from whole blood, wherein the separating step further comprises the steps of: collecting 10 ml of the whole blood from an animal or patient into a vacuum test tube containing 3.2% sodium citrate, and primarily centrifuging the collected whole blood at 1,750-1,900 g for 3 to 5 minutes; collecting a supernatant liquid comprising a plasma layer with a buffy coat obtained from said centrifugation; transferring the collected supernatant liquid to a new vacuum test tube by a blunt needle, and secondarily centrifuging the collected supernatant liquid at 4,500-5,000 g for 4 to 6 minutes; and collecting the PRP concentrated in a bottom layer by another blunt needle; mixing 1 mL of the PRP collected from the separating step with a calcium chloride solution with a concentration of 0.30-0.55 mg/mL by a three-way connector; and mixing a mixture of the PRP and the calcium chloride solution with type I collagen, wherein the mixing step of mixing the mixture of the PRP and the calcium chloride solution with the type I collagen further comprises the steps of: leaving the type I collagen at a room temperature for 15 to 30 minutes before mixing; and mixing the mixture of the PRP and the calcium chloride solution with the type I collagen with a concentration of 20-50 mg/mL, in an opaque phase, four times by another three-way connector. In some embodiments administration of fibroblasts is performed together with biocompatible polymers and growth factors or PRP, or Platelet Gel.

In one embodiment, allogeneic fibroblasts are obtained from a screened donor(s) using similar methods as described above. In this embodiment, a screened donor provides tissue for expansion of fibroblasts and generation of a master cell bank (MCB). After appropriate tests are conducted on the MCB, cells expanded from the master bank are used to create a working cell bank (WCB), which is in turn expanded for manufacture of conditioned media for use in the formulation of the allogeneic topical product. Reprogrammed cells possess a normal karyotype, differentiate into beating cardiomyocytes in vitro and differentiate into representatives of all three germ layers in vivo. A subpopulation of human dermal fibroblasts that express the pluripotency marker SSEA3 demonstrates enhanced iPSC generation efficiency as described by Bryne, et al., PLoS One, 4(9): e7118 (2009). SSEA3-positive and SSEA3-negative populations were transduced with the same retroviral vectors, under identical experimental conditions, and seeded onto inactivated mouse embryonic fibroblasts (MEFs). After three weeks of culture under standard hESC conditions, plates were examined in a double-blind analysis by three independent hESC biologists for iPSC colony formation. Colonies with iPSC morphology were picked and expanded. All three biological replicates with the transduced SSEA3-negative cells formed many large background colonies (10-27 per replicate) but no iPSC colonies emerged; in contrast, all three biological replicates with the transduced SSEA3-positive cells resulted in the formation of iPSC colonies (4-5 per replicate) but very few large background colonies (0-1 per replicate). Further characterization of the cell lines derived from the iPSC-like colonies showed that they possessed hESC-like morphology, growing as flat colonies with large nucleo-cytoplasmic ratios, defined borders and prominent nucleoli. When five lines were further expanded and characterized, all demonstrated expression of key pluripotency markers expressed by hESCs, which included alkaline phosphatase, Nanog, SSEA3, SSEA4, TRA160 and TRA181. The SSEA3-selected iPSCs also demonstrated a normal male karyotype (46, XY), the ability to differentiate into functional beating cardiomyocytes in vitro and differentiate into representatives of all three germ layers in vivo. Because no iPSC colony formation or line derivation from the transduced SSEA3-negative cells was observed, this indicates that these cells possess significantly lower or even no reprogramming potential relative to the SSEA3-expressing cells. Additionally, a 10-fold enrichment of primary fibroblasts that strongly express SSEA3 results in a significantly greater efficiency (8-fold increase) of iPSC line derivation compared to the control derivation rate ($p<0.05$). The SSEA3-positive cells appeared indistinguishable, morphologically, from the SSEA3-negative fibroblasts; furthermore, expression of the SSEA3 antigen is not considered a marker of other cell types such as mesenchymal or epidermal adult stem cells.

In one embodiment of the disclosure, platelet rich plasma is used to activate a rare subpopulation of SSEA3-expressing cells that exists in the dermis of adult human skin and may be isolated accordingly. These SSEA3-expressing cells undergo a significant increase in cell number in response to injury, indicating a role in regeneration. These SSEA3-expressing regeneration-associated (SERA) cells were derived through primary cell culture, purified by fluorescence activated cell sorting (FACS) and characterized. The SERA cells demonstrated a global transcriptional state most similar to bone marrow and fat derived mesenchymal stem cells (MSCs) and the highest expressing SSEA3 expressing cells co-expressed CD105. However, these cells cannot differentiate into adipocytes, osteoblasts or chondrocytes.

Treatment of individuals with lower back pain may be accomplished through one embodiment of the disclosure, such as through the administration of fibroblast cells that have been genetically modified to upregulate expression of angiogenic stimuli or anti-inflammatory activities. It is known in the art that genes may be introduced by a wide range of approaches including adenoviral, adeno-associated, retroviral, alpha-viral, lentiviral, Kunjin virus, or HSV vectors, liposomal, nano-particle mediated as well as electroporation and Sleeping Beauty transposons. Genes with angiogenic stimulatory function that may be transfected include but are not limited to: VEGF, FGF-1, FGF-2, FGF-4, EGF, HGF, and a combination thereof. Additionally, transcription factors that are associated with upregulating expression of angiogenic cascades may also be transfected into cells used for treatment of lower back pain, including: HIF-1alpha, HIF-2, NET, NF-kB, or a combination thereof. Genes inhibitory to inflammation may be used such as: TGF-a, TGF-b, IL-4, IL-10, IL-13, IL-20 thrombospondin, or a combination thereof, for example. Transfection may also be utilized for administration of genetic manipulation means in a manner to substantially block transcription or translation of genes which inhibit angiogenesis. Antisense oligonucleotides, ribozymes or short interfering RNA may be transfected into cells for use for treatment of lower back pain in order to block expression of antiangiogenic proteins such as: canstatin, IP-10, kringle 1-5, and collagen XVIII/endostatin, for example. Additionally, gene inhibitory technologies may be used for blocking ability of cells to be used for treatment of lower back pain to express inflammatory proteins including: IL-1, TNF-alpha, IL-2, IL-6, IL-8, IL-9, IL-11, IL-12, IL-15, IL-17, IL-18, IL-21, IL-23, IL-27, IFN-alpha, IFN-beta, and IFN-gamma. Globally acting transcription factors associated with inflammation may also be substantially blocked using not only the genetic means described but also decoy oligonucleotides. Suitable transcription factors for blocking include various subunits of the NF-kB complex such as p55, and/or p60, STAT family members, particularly STAT1, STAT5, STAT4, and members of the Interferon Regulatory Factor family such as IRF-1, IFR-3, and IFR-8, for example. Enhancement of angiogenic stimulation ability of the cells useful for the treatment of back pain can be performed through culturing under conditions of restricted oxygen. It is known in the art that stem cells in general, and ones with angiogenesis promoting activity specifically, tend to reside in hypoxia niches of the bone marrow. When stem cells differentiate into more mature progeny, they progressively migrate to areas of the bone marrow with higher oxygen tension.[40]. This important variable in tissue culture was used in studies that demonstrated superior expansion of human CD34 stem cells capable of full hematopoietic reconstitution were obtained in hypoxic conditions using oxygen tension as low as 1.5%. The potent expansion under hypoxia, which was 5.8-fold higher as compared to normal oxygen tension was attributed to hypoxia induction of HIF-1 dependent growth factors such as VEGF, which are potent angiogenic stimuli when released under controlled conditions [41]. Accordingly, culture of cells to be used for treatment of back pain may be performed in conditions of oxygen ranging from 0.5% to 4%, such as 1%-3% and including from 1.5%-1.9%. Hypoxia culture is not limited towards lowering oxygen tension but may also include administration of molecules that inhibit oxygen uptake or compete with oxygen uptake during the tissue culture process. Additionally, in an embodiment of the disclosure, hypoxia is induced through induction of one or more agents that cause the upregulation of the HIF-1 transcription factor.

In embodiments wherein the fibroblasts are exposed to hypoxia, the oxygen levels may be between 0.1%-5%, 0.1%-4%, 0.1%-3%, 0.1%-2%, 0.1%-1%, 0.1%-0.75%, 0.1%-0.5%, 0.1%-0.25%, 0.2%-5%, 0.2%-4%, 0.2%-3%, 0.2%-2%, 0.2%-1%, 0.2%-0.75%, 0.2%-0.5%, 0.5%-5%, 0.5%-4%, 0.5%-3%, 0.5%-2%, 0.5%-1%, 0.5%-0.75%, 0.75%-5%, 0.75%-4%, 0.75%-3%, 0.75%-2%, 0.75%-1%, 1%-5%, 1%-4%, 1%-3%, 1%-2%, 2%-5%, 2%-4%, 2%-3%, 3%-5%, 3%-4%, or 4%-5%% oxygen, in specific embodiments. The duration of exposure of the cells to hypoxic conditions, including with (but not limited to) these representative levels of oxygen, may be for a duration of 30 minutes (min)-3 days, 30 min-2 days, 30 min-1 day, 30 min-12 hours (hrs), 30 min-8 hrs, 30 min-6 hrs, 30 min-4 hrs, 30 min-2 hrs, 30 min-1 hour (hr), 1 hr-3 days, 1 hr-2 days, 1 hr-1 day, 1-12 hrs, 1-8 hrs, 1-6 hrs, 1-4 hrs, 1-2 hrs, 2 hrs-3 days, 2 hrs-2 days, 2 hrs-1 day, 2 hrs-12 hrs, 2-10 hrs, 2-8 hrs, 2-6 hrs, 2-4 hrs, 2-3 hrs, 6 hrs-3 days, 6 hrs-2 days, 6 hrs-1 day, 6-12 hrs, 6-8 hrs, 8 hrs-3 days, 8 hrs-2 days, 8 hrs-1 day, 8-16 hrs, 8-12 hrs, 8-10 hrs, 12 hrs-3 days, 12 hrs-2 days, 12 hrs-1 day, 12-18 hrs, 12-14 hrs, 1-3 days, or 1-2 days, as examples only.

Subsequent to various culture procedures, cells generated may be tested for angiogenic and/or anti-inflammatory activity before use in clinical conditions, in specific embodiments. Testing may be performed by various means known to one skilled in the art. In terms of assessing angiogenic potential the means include, but are not limited to: a) Ability to support endothelial cell proliferation in vitro using human umbilical vein endothelial cells or other endothelial populations (Assessment of proliferation may be performed using tritiated thymidine incorporation or by visually counted said proliferating endothelial cells. A viability dye such as MTT or other commercially available indicators may be used); b) Ability to support cord formation in subcutaneously implanted matrices (The matrices, which may include Matrigel or fibrin gel, for example, are loaded with cells generated as described above and implanted subcutaneously in an animal. The animal may be an immunodeficient mouse such as a SCID or nude mouse in order to negate immunological differences. Subsequent to implantation formation of endothelial cords may be assessed visually by microscopy. In order to distinguish cells stimulating angiogenesis versus host cells responding to said cells stimulating angiogenesis, a species-specific marker may be used); c) Ability to accelerate angiogenesis occurring in the embryonic chicken chorioallantoic membrane assay (Cells may be implanted directly, or via a matrix, into the chicken chorioallantoic membrane on embryonic day 9 and cultured for a period of approximately 2 days. Visualization of angiogenesis may be performed using in vivo microscopy); and/or d) Ability to stimulate neoangiogenesis in the hind limb ischemia model described above.

Assessment of the anti-inflammatory abilities of fibroblast cells generated or isolated for potential clinical use may also be performed. Numerous methods are known in the art, for example they may include assessment of the putative anti-inflammatory fibroblast cells to modulate immunological parameters in vitro. Putative anti-inflammatory fibroblast cells may be co-cultured at various ratios with an immunological cell. The immunological cell may be stimulated with an activatory stimulus. The ability of the putative anti-inflammatory cell to inhibit, in a dose-dependent manner, production of inflammatory cytokines or to augment production of anti-inflammatory cytokines, may be used as an output system of assessing anti-inflammatory activity. Additional output parameters may include: proliferation, cytotoxic activity, production of inflammatory mediators, or upregulation of surface markers associated with activation. Cytokines assessed may include: IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, TNF, IFN and/or RANKL. Specific immunological cells may be freshly isolated or may be immortalized cell lines. The immunological cells may be: T cells, B cells, monocytes, macrophages, neutrophils, eosinophils, basophils, dendritic cells, natural killer cells, natural killer T cells, gamma delta-T cells, or a combination thereof. The immunological stimuli may include an antibody, a ligand, a protein, or another cells. Examples including: crosslinking antibodies to T cell receptor, to costimulatory molecules such as CD28, to activation associated molecules such as CD69 or to receptors for stimulatory cytokines such as IL-2. Additional examples of inflammatory stimuli may include co-culture with allogeneic stimulator cells such as in mixed lymphocyte reactions, or may include stimulation with a non-specific activator such as a lectin. Specific lectins may include conconavalin-A, phytohemagluttinin, or wheat germ agglutinin. Other non-specific stimulators may be activators of the toll like receptor pathway such as lipopolysaccharide, CpG DNA motifs or bacterial membrane fractions. The methods described in the above two paragraphs are shown only as examples that may be used to determine, before entry into clinical use, whether a cell population generated as described in the present invention is capable of producing the desired angiogenic stimulatory or anti-inflammatory effects. These examples are only provided as guides which one skilled in the art can optimize upon using routine experimentation.

For any embodiments of the disclosure provided herein, cells to be used for treatment of lower back pain may be cryopreserved for subsequent use, as well as for transportation, in some cases. One skilled in the art knows numerous methods of cellular cryopreservation. Typically, cells may be treated to a cryoprotection process, then stored frozen until needed. Once needed cells require specialized care for revival and washing to clear cryopreservative agents that may have detrimental effects on cellular function. Generally, cryopreservation requires attention be paid to three main concepts, these are: 1) the cryoprotective agent, 2) the control of the freezing rate, and 3) the temperature at which the cells will be stored. Cryoprotective agents are well known to one skilled in the art and can include but are not limited to dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, or choline chloride as described in U.S. Pat. No. 6,461,645 (incorporated by reference herein in its entirety), for example. A method for cryopreservation of cells that is utilized by some skilled artisans comprises DMSO at a concentration not being immediately cytotoxic to cells under conditions which allow it to freely permeate the cell and to protect intracellular organelles; the DMSO combines with water and prevents cellular damage induced from ice crystal formation. Addition of plasma at concentrations between 20-25% by volume can augment the protective effect of DMSO. After addition of DMSO, cells should be kept at temperatures below 4 C, in order to prevent DMSO-mediated damage. Methods of actually inducing the cells in a state of suspended animation involve utilization of various cooling protocols. While cell type, freezing reagent, and concentration of cells are important variables in determining methods of cooling, it is generally accepted that a controlled, steady rate of cooling is optimal. There are numerous devices and apparatuses known in the field that are capable of reducing temperatures of cells for optimal cryopreservations. One such apparatus is the Thermo Electro Cryomed Freezer™ manufactured by Thermo Electron Corporation. Cells can also be frozen in CryoCyte™ containers as made by Baxter. One example of cryopreservation is as follows: $2 \times 10^6$ CD34 cells/ml are isolated from cord blood using the Isolex System™ as per manufacturer's instructions (Baxter). Cells are incubated in DMEM media with 10% DMSO and 20% plasma. Cooling is performed at 1 Celsius./minute from 0 to −80 Celsius. When cells are needed for use, they are thawed rapidly in a water bath maintained at 37 Celsius water bath and chilled immediately upon thawing. Cells are rapidly washed, either a buffer solution, or a solution containing a growth factor. Purified cells can then be used for expansion if needed. A database of stored cell information (such as donor, cell origination types, cell markers, etc.) can also be prepared, if desired.

In certain embodiments, fibroblasts may be derived from tissues comprising skin, heart, blood vessels, bone marrow, skeletal muscle, liver, pancreas, brain, adipose tissue, foreskin, placental, and/or umbilical cord, for example. In specific embodiments, the fibroblasts are placental, fetal, neonatal or adult or mixtures thereof.

The number of administrations of cells to an individual will depend upon the factors described herein at least in part and may be optimized using routine methods in the art. In specific embodiments, a single administration is required. In other embodiments, a plurality of administration of cells is required. It should be appreciated that the system is subject to variables, such as the particular need of the individual, which may vary with time and circumstances, the rate of loss of the cellular activity as a result of loss of cells or activity of individual cells, and the like. Therefore, it is expected that each individual could be monitored for the proper dosage, and such practices of monitoring an individual are routine in the art.

In some embodiments, the cells are subjected to one or more media compositions that comprises, consists of, or consists essentially of Roswell Park Memorial Institute (RPMI-1640), Dublecco's Modified Essential Media (DMEM), Eagle's Modified Essential Media (EMEM), Optimem, Iscove's Media, or a combination thereof.

In particular cases, the fibroblasts are recombinantly manipulated to encode SSEA3, VEGF, FGF-1, FGF-2, FGF-4, EGF, HGF, HIF-1alpha, HIF-2, NET, NF-kB, TGF-a, TGF-b, IL-4, IL-10, IL-13, IL-20 thrombospondin, canstatin, IP-10, kringle 1-5, collagen XVIII/endostatin, IL-1, TNF-alpha, IL-2, IL-6, IL-8, IL-9, IL-11, IL-12, IL-15, IL-17, IL-18, IL-21, IL-23, IL-27, IFN-alpha, IFN-beta, IFN-gamma, p55, p60, STAT1, STAT5, STAT4, IRF-1, IFR-3, IFR-8, or a combination thereof. In cases wherein recombination technology is employed, one or more types of the fibroblast cells are manipulated to harbor one or more expression vectors that each encode one or more gene products of interest. A recombinant expression vector(s) can be introduced as one or more DNA molecules or constructs, where there may be at least one marker that will allow for selection of host cells that contain the vector(s). The vector(s) can be prepared in conventional ways, wherein the genes and regulatory regions may be isolated, as appropriate, ligated, cloned in an appropriate cloning host, and analyzed by sequencing or other convenient means. Particularly, using PCR, individual fragments including all or portions of a functional unit may be isolated, where in some cases one or more mutations may be introduced using "primer repair", ligation, in vitro mutagenesis, etc. as appropriate. The vector(s) once completed and demonstrated to have the appropriate sequences may then be introduced into the host cell by any convenient means. The constructs may be integrated and packaged into non-replicating, defective viral genomes like lentivirus, Adenovirus, Adeno-associated virus (AAV), Herpes simplex virus (HSV), or others, including retroviral vectors, for infection or transduction into cells. The vector(s) may include viral sequences for transfection, if desired. Alternatively, the construct may be introduced by fusion, electroporation, biolistics, transfection, lipofection, or the like. The host cells may be grown and expanded in culture before introduction of the vector(s), followed by the appropriate treatment for introduction of the vector(s) and integration of the vector(s). The cells are then expanded and screened by virtue of a marker present in the construct. Various markers that may be used successfully include hprt, neomycin resistance, thymidine kinase, hygromycin resistance, etc.

Any of the genes or gene products described herein, or active portions thereof, may be cloned into mammalian expression constructs comprising one or more promoter sequences enabling expression in cells such as the CMV promoter [Artuc et al., Exp. Dermatol. 1995, 4:317-21]. Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available, or the pSH expression vector which enables a regulated polynucleotide expression in human foreskin cells [Ventura and Villa, 1993, *Biochem. Biophys. Commun.* 192: 867-9]. Examples of retroviral vector and packaging systems are those sold by Clontech, San Diego, Calif., USA, including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter. After completing plasmid transfection fibroblasts are harvested by a means allowing for detachment from tissue culture plates, for example, by trypsinization and transferred to either a 6-well (Nunc, Denmark) or a 24-well plate (Nunc) for proliferation. Approximately 3 days post-transfection, the cell media is changed to media allow for proliferation and expansion of modified fibroblasts. One example is Neurobasal A (NBA) proliferation medium comprising Neurobasal-A (Invitrogen), 1% D-glucose (Sigma Aldrich), 1% Penicillin/Streptomycin/Glutamine (Invitrogen), 2% B27 supplement with Retinoic acid (Invitrogen), 0.2% EGF (Peprotech, USA), 0.08% FGF-2 (Peprotech), 0.2% Heparin (Sigma Aldrich, USA) and Valproic acid (Sigma-Aldrich) to a concentration of 1 □M. The media is then subsequently changed thrice weekly, and cells are re-plated regularly (for example, 2-8 times up to a maximum of weekly re-plating, becoming more regular as colonies began to develop) to remove non-reprogrammed cells until widespread colony formation is achieved.

In some instances, one or more agents may be introduced into the cells as an RNA molecule for transient expression.

RNA can be delivered to any cells, including any modified cells, of the disclosure by various means including microinjection, electroporation, and lipid-mediated transfection, for example. In particular aspects, introduction of vector(s) into cells may occur via transposons. An example of a synthetic transposon for use is the Sleeping Beauty transposon that comprises an expression cassette including the angiogenic agent gene thereof. Alternatively, one may have a target site for homologous recombination, where it is desired that vector(s) be integrated at a particular locus using materials and methods as are known in the art for homologous recombination. For homologous recombination, one may use either OMEGA or O-vectors. See, for example, Thomas and Capecchi, 1987; Mansour, et al., 1988; and Joyner, et al., 1989.

The vector(s) may be introduced as a single DNA molecule encoding at least one agent (including one or more tumor inhibitory agents or functional fragments thereof) and optionally another polynucleotide (such as genes), or different DNA molecules having one or more polynucleotides (such as genes). The vector(s) may be introduced simultaneously or consecutively, each with the same or different markers. In an illustrative example, one vector would contain one or more agents (such as angiogenic agent(s)) under the control of particular regulatory sequences.

Vector(s) comprising useful elements such as bacterial or yeast origins of replication, selectable and/or amplifiable markers, promoter/enhancer elements for expression in prokaryotes or eukaryotes, etc. that may be used to prepare stocks of vector DNAs and for carrying out transfections are well known in the art, and many are commercially available.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In some situations, it may be desirable to kill the modified cells, such as when the object is to terminate the treatment, the cells become neoplastic, in research where the absence of the cells after their presence is of interest, and/or another event. For this purpose one can provide for the expression of certain gene products in which one can kill the modified cells under controlled conditions, such as a suicide gene. Suicide genes are known in the art, e.g. the iCaspase9 system in which a modified form of caspase 9 is dimerizable with a small molecule, e.g. AP1903. See, e.g., Straathof et al., *Blood* 105:4247-4254 (2005).

EXAMPLES

The following examples are presented in order to more fully illustrate the preferred embodiments of the invention. They should in no way, however, be construed as limiting the broad scope of the invention.

Example 1

Culture with Platelet Rich Plasma Enhances Immune Suppressive Marker PD-1L Expression of Fibroblasts Fibroblasts are cultured with platelet rich plasma (PRP) to produce enhanced fibroblasts for therapeutic use. Foreskin fibroblasts, human bone marrow MSC and human adipose MSC were obtained from ATCC and cultured in DMEM media containing 10% fetal calf serum in the concentrations of PRP noted in FIG. 1 that were generated from a healthy donor. Cells were cultured for 48 hours. PD-anti PDL1-PE or isotype control (Becton Dickenson, Franklin Lakes, N.J.) was used for staining according to the manufacturer's instructions. The live/dead fixable near-infrared dye (Invitrogen) was used to exclude dead cells. Fluorescence of the viable cells gated was quantified as Mean Fluorescent Intensity (MFI). As seen in FIG. 1, increase in PD-L1 expression was observed uniquely in fibroblasts.

Example 2

Culture with Platelet Rich Plasma Enhances Ability of Fibroblasts to Suppress T Cell Activation Fibroblasts are cultured with PRP to produce enhanced fibroblasts for therapeutic use. Foreskin fibroblasts, human bone marrow MSC and human adipose MSC were obtained from ATCC and cultured in DMEM media containing 10% fetal calf serum in the following concentrations of platelet rich plasma (PRP) generated from a healthy donor. Cells were cultured for 48 hours. Subsequently cells were plated with allogeneic peripheral blood mononuclear cells stimulating with 0.5 micrograms per ml of phytohemagglutinin. Cells were co-cultured for 72 hours with 1 microCurie of tritiated thymidine added in the last 12 hours of culture. Proliferation was assessed by scintillation counting. As observed, addition of PRP uniquely enhanced immune suppressive activity of fibroblasts.

Example 3

Culture with Platelet Rich Plasma Enhances Ability of Fibroblasts to Suppress T Cell Production of Interferon Gamma Fibroblasts are cultured with platelet rich plasma (PRP) to produce enhanced fibroblasts for therapeutic use. Foreskin fibroblasts, human bone marrow MSC and human adipose MSC were obtained from ATCC and cultured in DMEM media containing 10% fetal calf serum in the following concentrations of platelet rich plasma (PRP) generated from a healthy donor. Cells were cultured for 48 hours. Subsequently, cells were plated with allogeneic peripheral blood mononuclear cells stimulating with 0.5 micrograms per ml of phytohemagglutinin. Cells were co-cultured for 48 hours and assessment of interferon gamma production was performed by ELISA. As observed, a decrease in interferon gamma production was observed uniquely in the PRP treated fibroblasts.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

Patents

U.S. Pat. No. 5,165,928
U.S. Pat. No. 5,585,007

U.S. Pat. No. 5,599,558
U.S. Pat. No. 5,614,204
U.S. Pat. No. 6,010,627
U.S. Pat. No. 6,214,338
U.S. Pat. No. 6,303,112
U.S. Pat. No. 6,461,645
U.S. Pat. No. 6,649,072
U.S. Pat. No. 9,011,929

Publications

1. Frymoyer J W, D. C., *The economics of spinal disorders.* In Frymoyer J W, Ducker T B, Hadler N M, et al., eds. *The adult spine: principles and practice.* Philadelphia, Pa.: Lippincott-Raven, 1997: 143-50.
2. Lively, M. W., *Sports medicine approach to low back pain.* South Med J, 2002. 95(6): p. 642-6.
3. Hart, L. G., R. A. Deyo, and D. C. Cherkin, *Physician office visits for low back pain. Frequency, clinical evaluation, and treatment patterns from a U.S. national survey.* Spine, 1995. 20(1): p. 11-9.
4. Peng, B., et al., *Possible pathogenesis of painful intervertebral disc degeneration.* Spine, 2006. 31(5): p. 560-6.
5. Freemont, A. J., et al., *Nerve ingrowth into diseased intervertebral disc in chronic backpain.* Lancet, 1997. 350(9072): p. 178-81.
6. Schwarzer, A. C., et al., *The prevalence and clinical features of internal disc disruption in patients with chronic low back pain.* Spine, 1995. 20(17): p. 1878-83.
7. Saifuddin, A., et al., *The value of lumbar spine magnetic resonance imaging in the demonstration of anular tears.* Spine, 1998. 23(4): p. 453-7.
8. Ito, M., et al., *Predictive signs of discogenic lumbar pain on magnetic resonance imaging with discography correlation.* Spine, 1998. 23(11): p. 1252-8; discussion 1259-60.
9. Moneta, G. B., et al., *Reported pain during lumbar discography as a function of anular ruptures and disc degeneration. A re-analysis of 833 discograms.* Spine, 1994. 19(17): p. 1968-74.
10. Peng, B., et al., *The pathogenesis of discogenic low back pain.* J Bone Joint Surg Br, 2005. 87(1): p. 62-7.
11. Benoist, M., Natural history of the aging spine. Eur Spine J, 2003. 12 Suppl 2: p. S86-9.
12. Urban, J. P., et al., *Nutrition of the intervertebral disk. An in vivo study of solute transport.* Clin Orthop Relat Res, 1977(129): p. 101-14.
13. Konttinen, Y. T., et al., *Transforming and epidermal growth factors in degenerated intervertebral discs.* J Bone Joint Surg Br, 1999. 81(6): p. 1058-63.
14. Razaq, S., R. J. Wilkins, and J. P. Urban, *The effect of extracellular pH on matrix turnover by cells of the bovine nucleus pulposus.* Eur Spine J, 2003. 12(4): p. 341-9.
15. Gruber, H. E., J. A. Ingram, and E. N. Hanley, Jr., *Immunolocalization of MMP-19 in the human intervertebral disc: implications for disc aging and degeneration.* Biotech Histochem, 2005. 80(3-4): p. 157-62.
16. Seguin, C. A., et al., *Tumor necrosis factor-alpha modulates matrix production and catabolism in nucleus pulposus tissue.* Spine, 2005. 30(17): p. 1940-8.
17. Omlor, G. W., et al., *Changes in gene expression and protein distribution at different stages of mechanically induced disc degeneration—an in vivo study on the New Zealand white rabbit.* J Orthop Res, 2006. 24(3): p. 385-92.
18. Hwang, G. J., et al., *Contrast enhancement pattern and frequency of previously unoperated lumbar discs on MRI.* J Magn Reson Imaging, 1997. 7(3): p. 575-8.
19. Levicoff, E. A., L. G. Gilbertson, and J. D. Kang, *Gene therapy for disc repair.* Spine J, 2005. 5(6 Suppl): p. 287S-296S.
20. Yoon, S. T., *Molecular therapy of the intervertebral disc.* Spine J, 2005. 5(6 Suppl): p. 280S-286S.
21. Masuda, K., T. R. Oegema, Jr., and H. S. An, *Growth factors and treatment of intervertebral disc degeneration.* Spine, 2004. 29(23): p. 2757-69.
22. Shimer, A. L., et al., *Gene therapy approaches for intervertebral disc degeneration.* Spine, 2004. 29(23): p. 2770-8.
23. Setton, L. A. and J. Chen, *Cell mechanics and mechanobiology in the intervertebral disc.* Spine, 2004. 29(23): p. 2710-23.
24. Roughley, P. J., *Biology of intervertebral disc aging and degeneration: involvement of the extracellular matrix.* Spine, 2004. 29(23): p. 2691-9.
25. Roberts, S., et al., *Matrix metalloproteinases and aggrecanase: their role in disorders of the human intervertebral disc.* Spine, 2000. 25(23): p. 3005-13.
26. Nagase, H. and J. F. Woessner, Jr., *Matrix metalloproteinases.* J Biol Chem, 1999. 274(31): p. 21491-4.
27. Wallach, C. J., et al., *Gene transfer of the catabolic inhibitor TIMP-1 increases measured proteoglycans in cells from degenerated human intervertebral discs.* Spine, 2003. 28(20): p. 2331-7.
28. Zhan, Z., et al., *Ad/CMV-hTGF-beta1 treats rabbit intervertebral discs degeneration in vivo.* J Huazhong Univ Sci Technolog Med Sci, 2004. 24(6): p. 599-601, 624.
29. Thompson, J. P., T. R. Oegema, Jr., and D. S. Bradford, *Stimulation of mature canine intervertebral disc by growth factors.* Spine, 1991. 16(3): p. 253-60.
30. Yoon, S. T., et al., *ISSLS prize winner: LMP-1 upregulates intervertebral disc cell production of proteoglycans and BMPs in vitro and in vivo.* Spine, 2004. 29(23): p. 2603-11.
31. Kim, K. S., et al., *Inhibition of proteoglycan and type II collagen synthesis of disc nucleus cells by nicotine.* J Neurosurg, 2003. 99(3 Suppl): p. 291-7.
32. Masuda, K., et al., *Recombinant osteogenic protein-1 upregulates extracellular matrix metabolism by rabbit annulus fibrosus and nucleus pulposus cells cultured in alginate beads.* J Orthop Res, 2003. 21(5): p. 922-30.
33. Zhang, Y., et al., *Growth factor osteogenic protein-1: differing effects on cells from three distinct zones in the bovine intervertebral disc.* Am J Phys Med Rehabil, 2004. 83(7): p. 515-21.
34. Takegami, K., et al., *Osteogenic protein-1 enhances matrix replenishment by intervertebral disc cells previously exposed to interleukin-1.* Spine, 2002. 27(12): p. 1318-25.
35. Chang, S. C., et al., *Cartilage-derived morphogenetic proteins. New members of the transforming growth factor-beta superfamily predominantly expressed in long bones during human embryonic development.* J Biol Chem, 1994. 269(45): p. 28227-34.
36. Eppley, B. L., J. E. Woodell, and J. Higgins, *Platelet quantification and growth factor analysis from platelet-rich plasma: implications for wound healing.* Plast Reconstr Surg, 2004. 114(6): p. 1502-8.
37. Jenis, L. G., R. J. Banco, and B. Kwon, *A prospective study of Autologous Growth Factors (AGF) in lumbar interbody fusion.* Spine J, 2006. 6(1): p. 14-20.

38. Kevy, S. V. and M. S. Jacobson, *Comparison of methods for point of care preparation of autologous platelet gel.* J Extra Corpor Technol, 2004. 36(1): p. 28-35.
39. Vadala, G., et al., *A clinically relevant hydrogel based on hyaluronic acid and platelet rich plasma as a carrier for mesenchymal stem cells: Rheological and biological characterization.* J Orthop Res, 2016.
40. Ivanovic, Z., et al., *Hypoxia maintains and interleukin-3 reduces the pre-colony-forming cell potential of dividing CD34(+) murine bone marrow cells.* Exp Hematol, 2002. 30(1): p. 67-73.
41. Danet, G. H., et al., *Expansion of human SCID-repopulating cells under hypoxic conditions.* J Clin Invest, 2003. 112(1): p. 126-35.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of generating regenerative fibroblasts comprising the step of contacting fibroblasts with platelet-rich plasma and one or more biologically active substances, thereby generating regenerative fibroblasts having improved anti-inflammatory activity compared to fibroblasts that lack said contact, wherein the one or more biologically active substances comprise hyaluronic acid and batroxobin.

2. The method of claim 1, wherein said biologically active substance comprises one or more cytokines.
3. The method of claim 2, wherein said cytokine comprises one or more growth factors.
4. The method of claim 3, wherein said growth factor is FGF-alpha.
5. The method of claim 3, wherein said growth factor is FGF-beta.
6. The method of claim 3, wherein said growth factor is a member of the TGF-beta family.
7. The method of claim 1, wherein the fibroblast cells are selected from the group consisting of (a) fibroblasts obtained by biopsy, cultured and proliferated; (b) subsets thereof having greater ability to differentiate; and (c) a combination thereof.
8. The method of claim 1, wherein the fibroblasts express stage specific embryonic antigen 3 (SSEA3).
9. The method of claim 1, wherein said fibroblasts are comprised in a pharmaceutically acceptable carrier selected from the group consisting of sterile solutions, hydrogels, implantable cell matrices, devices and a combination thereof.
10. The method of claim 1, wherein the fibroblasts are derived from tissues comprising skin, heart, blood vessels, bone marrow, skeletal muscle, liver, pancreas, brain, adipose tissue, foreskin, placental, and/or umbilical cord.
11. The method of claim 1, wherein the fibroblasts are placental, fetal, neonatal, adult or a combination thereof.
12. The method of claim 1, wherein a therapeutically effective amount of the fibroblasts are provided to the disc of an individual in need of disc repair.
13. The method of claim 1, wherein the fibroblasts are recombinantly manipulated to encode SSEA3, VEGF, FGF-1, FGF-2, FGF-4, EGF, HGF, HIF-1alpha, HIF-2, NET, NF-kB, TGF-a, TGF-b, IL-4, IL-10, IL-13, IL-20 thrombospondin, canstatin, IP-10, kringle 1-5, collagen XVIII/endostatin, IL-1, TNF-alpha, IL-2, IL-6, IL-8, IL-9, IL-11, IL-12, IL-15, IL-17, IL-18, IL-21, IL-23, IL-27, IFN-alpha, IFN-beta, IFN-gamma, p55, p60, STAT1, STATS, STAT4, IRF-1, IFR-3, IFR-8, or a combination thereof.

* * * * *